United States Patent [19]

Baumann

[11] 4,184,843
[45] Jan. 22, 1980

[54] COMPOSITION FOR DYEING HAIR CONTAINING DISPERSE DYES AND A THICKENING AGENT

[75] Inventor: Hans Baumann, Arild, Sweden

[73] Assignee: Carl Viktor Danielson, Astorp, Sweden

[21] Appl. No.: 823,913

[22] Filed: Aug. 12, 1977

[30] Foreign Application Priority Data

Aug. 31, 1976 [SE] Sweden ............................ 7609628

[51] Int. Cl.$^2$ .............................................. A61K 7/13
[52] U.S. Cl. .................................... 8/10.1; 8/10; 8/86; 8/89 R; 8/92; 8/93; 8/94 R
[58] Field of Search ................... 8/10, 10.1, 86, 89, 8/92, 93, 94

[56] References Cited

U.S. PATENT DOCUMENTS

| | | |
|---|---|---|
| 3,098,013 | 7/1963 | Austin et al. ............. 8/10.1 |
| 3,168,441 | 2/1965 | Bil et al. .................. 8/10.1 |
| 3,206,363 | 9/1965 | Lecher et al. ............. 8/10.1 |
| 3,369,970 | 2/1968 | McLaughlin et al. ....... 8/10.1 |
| 3,586,475 | 6/1971 | Hewitt ...................... 8/10.1 |

FOREIGN PATENT DOCUMENTS

| | | | |
|---|---|---|---|
| 84838 | 1/1958 | Denmark ................................ 8/10.1 |
| 1212684 | 3/1966 | Fed. Rep. of Germany ............ 8/10.1 |
| 191221 | 9/1964 | Sweden ................................... 8/10.1 |
| 210140 | 1/1967 | Sweden ................................... 8/10.1 |
| 320766 | 2/1970 | Sweden ................................... 8/10.1 |

*Primary Examiner*—James O. Thomas, Jr.
*Assistant Examiner*—Vera C. Clarke
*Attorney, Agent, or Firm*—Eric Y. Munson

[57] ABSTRACT

A composition for dyeing human hair, in which a dispersion dye, preferably of the azo or anthraquinone type, is dispersed in an emulsified aqueous mixture comprising a paraffin component and a thickening agent component and adjusted to a pH not higher than 8 by addition of acid. The thickening agent component comprises fatty alcohols such as lauryl alcohol, cetyl alcohol, cetyl-stearyl alcohol or mixtures thereof, fatty acid esters such as isopropyl alcohol and a mixture of fatty acid mono- and diglycerides. The desired viscosity is imparted to the composition by adjusting the proportion of the paraffin component relative to the thickening agent component. An emulsifying agent, such as high-ethoxylated polyglycol ethers and diethanolamine phosphates may be added to create an emulsion of desired viscosity and permanence.

8 Claims, No Drawings

4,184,843

COMPOSITION FOR DYEING HAIR CONTAINING DISPERSE DYES AND A THICKENING AGENT

BACKGROUND OF THE INVENTION

In cosmetic technology there is today for light and wash resistant dyeing of human hair used practically only oxidation dyes, i.e. low molecular starting substances which are oxidized by means of $H_2O_2$ to the desired colour. These low molecular starting substances readily penetrate into the hair, are there oxidized to large dye molecules and in this way fixed mechanically. This well-known method yields good colouring results, but nevertheless it is an important desire by the hair cosmetic industry to be able to have it replaced by methods which are simpler and kinder to the hair. A composition which satisfies modern requirements should not contain $H_2O_2$ and should have a low pH value which today lies at a level as high as about 10.

An attempt in this direction has been to replace the oxidation dyes by dispersion dyes which are not water soluble but merely dispersible in water. These dyes, therefore, are not capable of penetrating appreciably into the hair even if the hair is strongly massaged in connection with the application of the dye. Where a mechanical fixing is possible a virtual dyeing process is required, which, however, starts only at an increased temperature, namely 40° to 50° C. Even if this temperature increase is moderate in itself and can easily be provided by usual heating means, for example by means of a heating hood, the actual dyeing thus takes place only during the heating of the hair. In this case a difficulty has been that one has not been able to apply sufficient amounts of the dyestuff in water-thin solution. This may be compensated for by making the dispersion more viscous, and attempts have also been made by means of thickening agents to obtain a composition which satisfies the condition of applying a sufficient amount of the dyestuff for the subsequent treatment at an increased temperature.

Up to now, however, one has not been successful in finding an acceptable thickening agent, since it must have suitable properties from a great many different aspects. By way of example it may be mentioned that thickening agents of the type of high molecular substances in most cases have a detrimental influence on the colouring in the heat treatment and/or produce deposits especially within the acid range. An exception from this is ammonium polyacrylate, which, however, on the other hand, is a pure glue and, therefore, affects the hair in an unfavourable way, in so far as it becomes rough and difficult to comb out even after vigorous rinsing.

Further, in hair dyeing preparations there are sometimes also used relatively highly concentrated surfactant solutions which in this concentration are viscous, for example nonyl phenols, or which become viscous after the addition of a slight percentage of common salt, for example shampoo, on the basis of ether sulfates. Nor are such viscous surfactant solutions suited for dispersion dyes. Even after heating, the dye particles in this environment adhere poorly to the hair apart from the fact that it is undesirable to let the skin come in contact with heated concentrated surfactant solution for a prolonged period of time.

OBJECTS OF THE INVENTION

Among the objects of the invention is to provide a composition which contains dispersion dye and thickening agent and through which the above-mentioned drawbacks have been entirely overcome. Accordingly, the hair dyeing shall be practicable while the composition has such a viscosity that during the application thereof it is retained on the hair through adhesion in a sufficient amount. Another object is to impart to the hair the desired shade from a light tinting to a stronger colouring effect which permanently remains in the hair, after the heat treatment has taken place and excess dye has been rinsed off from the hair. The structure of the hair will not be weakened by the dyeing, and will maintain its original properties with regard to softness and combing.

SUMMARY OF THE INVENTION

The invention is essentially characterized by the fact that dispersion dye, preferably of azo or anthraquinone type, respectively, for example Celliton dyes from BASF, are mixed with a thickening agent in aqueous dispersion, said agent consisting of an emulsion of fatty alcohol or fatty acid ester, respectively, in admixture with paraffins in solid or liquid form. The fatty alcohol preferably consists of $C_{10}$–$C_{30}$ alcohols, thus for example lauryl, cetyl-stearyl alcohol and the like, or mixtures thereof. The fatty acid esters consist of similar fatty acids and mono- or polyvalent alcohols, for example isopropyl alcohol or glycerol. Without being disadvantageously affected in other respects the composition may, by an addition of acid substances, get a pH value which is lower than 8 and preferably lies within the limits 5 to 3, which for various reasons is highly desirable.

Among a number of various substances, fatty alcohol, fatty acid ester and paraffin have already been proposed as thickening agents in hair dyeing compositions. These proposals have not led to any practically useful result by the fact that these substances individually make the effect of the dispersion dye on the hair more difficult or impede such effect, respectively, with the simultaneous fulfillment of the condition that the composition must possess high viscosity. The dye is not capable of adding to the hair but is rinsed off for the most part in a subsequent washing in water. This is true to a particularly high degree in respect of paraffin which, however, unexpectedly precisely together with fatty alcohol or fatty acid esters, respectively, gives the composition dyeing properties which are widely superior to those of a composition in which merely the lastmentioned component is contained.

Only by the combination of the two components—fatty alcohol or fatty acid ester, respectively, and paraffin—was it found possible to overcome this difficult and, thus, to solve the problem of dyeing hair by means of the dispersion dyes favourable in so many respects. The effect of the paraffin in the mixture on the dyeing procedure will probably have to do with interface processes in a 3-phase system. The hardly measurable 3-phase surface tension and diffusion constant plays a great part. It is found that the best dyeing result is obtained when the addition of paraffin is kept between 20 or 25 and 40 percentage by weight of the other component, i.e. the fatty alcohol and/or the fatty acid ester. The proportion of paraffin may be increased short of 100 % with a favourable result.

The emulsifying agent or the emulsifier contained in the composition is in the first place selected among nonionic surfactants, but also anionic surfactants may be added. Examples thereof are high-ethoxylated polyglycol ethers and diethanolamine phosphates, respectively. The purpose of the addition of emulsifiers is essentially to create an emulsion of the thickening agent with a desired viscosity and permanence.

The composition is given a viscosity within the range of 1,000 to 35,000 cP, depending upon secondary, hairdresser's technical points of view. Optimum dyeing effect is obtained in the range of 2,500 to 15,000 cP. Outside these limits the effect is slightly less but still satisfactory.

EXAMPLE 1

| | |
|---|---|
| Lauryl alcohol | 3,5% |
| Paraffin oil | 1,4% |
| Eumulgin B 1* | 1,4% |
| Dispersion dye brown, e.g. Celliton Bg braun | 4,0% |
| Citric acid or water ad 100 and pH 4,5, respectively; viscosity about | 1,500 cP. |

*Eumulgin B 1: Nonionic, high-ethoxylated fatty alcohol (Henkel) (emulsifier)

EXAMPLE 2

| | |
|---|---|
| Cetyl alcohol | 5,0% |
| Paraffin oil | 2,0% |
| Eumulgin B 1 | 2,0% |
| Brown dye as above | 4,0% |
| Citric acid and water ad 100 and pH 4,5, respectively | |
| Viscosity about 3,000 cP | |

EXAMPLE 3

| | |
|---|---|
| Cutina MD* | 6,0% |
| Paraffin oil | 2,0% |
| Eumulgin B 1 | 3,0% |
| Diethanolamine alkyl phosphate** | 2,0% |
| Brown dye as above | 4,0% |
| Viscosity about 3,000 cP | |

*Cutina MD: A mixture of fatty acid mono- and diglycerides (Henkel)
**Diethanolamine alkyl phosphate: Anionic surfactant (emulsifier)

EXAMPLE 4

| | | |
|---|---|---|
| Cutina MD | 8,0% | |
| Isopropyl myristate | 2,0% | (fatty acid ester) |
| Paraffin | 3,0% | |
| Eumulgin B 1 | 4,0% | |
| Brown dye as above | 4,0% | |
| Citric acid and water ad 100 and pH 3,5, respectively | | |
| Viscosity about 3,000 cP | | |

EXAMPLE 5

As example 4, but isopropyl myristate is replaced by 2 % Mygliol 812 (Nobel-Dynamit) = fatty acid ester, namely the triglyceride of $C_{10}$-$C_{12}$ fatty acids. Viscosity about 3,000 cP.

EXAMPLE 6

| | |
|---|---|
| Lanette O* | 10,0% |
| Paraffin oil | 4,0% |
| Eumulgin B1 | 4,0% |
| Brown dye as above | 5,0% |
| Citric acid and water ad 100 and pH 4, respectively | |
| Viscosity about 20,000 to 25,000 cP | |

*Lanette O: Cetyl-stearyl alcohol (Henkel)

After applying the liquid composition the hair is subjected to a heat treatment with a customary heating apparatus (heating hood, dark radiator etc.) at a temperature of 40° to 50° C. During this treatment the composition is not allowed to dry but has to maintain at least part of its moisture content. Therefore, during the treatment the air surrounding the hair shall have a high percentage of moisture. Thereupon an excess of the dye composition is washed off by means of water before further treatment (shampoo, drying etc.) takes place.

The fact that surfactant-containing emulsions give good dyeing results is not in contrast to what has been said earlier about pure, concentrated surfactant solutions. As will be seen from the examples the surfactants (emulsifiers) are used in low concentration. More particularly, only so much emulsifier is used that a durable emulsion is produced. In this condition the emulsifier is substantially changed also chemically, for example, it does no longer foam. Also the thickening is in the first place brought about through the emulsified substance, such as the fatty alcohol, not through the emulsifier. On the contrary, through excess of emulsifier a lowering of viscosity of the emulsion is brought about.

According to the invention there has been produced a composition which forms a commercially finished unit for immediate use and mixing of several components, as takes place in the case of the oxidation dye method used today, is disposed of. The pH of the dye may be kept low and due to the size of the particles contained in the dye the risk of penetration into the skin is practically eliminated. Dispersion hair dyes according to the invention not only produce uniform, satisfactory dyeing results but also have an excellent hair cosmetic effect. They lend a pleasant softness and lustre to the hair and make the combing easier.

I claim:

1. A composition for dyeing human hair, comprising a disperse dye dispersed in an aqueous mixture of an emulsifying agent, a paraffin component and a thickening agent selected from the group consisting of fatty alcohols having 10–30 carbon atoms and fatty acid esters of isopropyl alcohol and glycerol, the amount of the paraffin component relative to the thickening agent component being proportioned so as to impart to the composition a viscosity range between 100 cP and 35,000 cP, said composition being adjusted to a pH not higher than 8.

2. A composition according to claim 1, in which the disperse dye is selected from the group consisting of azo and anthraquinone dyes.

3. A composition according to claim 1, in which the pH is from 5 to 3.

4. A composition according to claim 1, in which the fatty alcohols are selected from the group consisting of lauryl alcohol, cetyl alcohol and stearyl alcohol.

5. A composition according to claim 1, in which the proportion of paraffin component relative to the thickening agent component by weight ranges between 20% and 40%.

6. A composition according to claim 5, in which the pH is from 5 to 3.

7. A composition according to claim 5, in which the disperse dye is selected from the group consisting of azo and anthraquinone dyes.

8. A composition according to claim 7, in which the pH of the composition is from 5 to 3.

* * * * *